(12) United States Patent
Donn et al.

(10) Patent No.: US 6,846,969 B2
(45) Date of Patent: *Jan. 25, 2005

(54) PROCESS FOR THE PRODUCTION OF PLANTS WITH ENHANCED GROWTH CHARACTERISTICS

(75) Inventors: Günter Donn, Hofheim (DE); Peter Eckes, Kelkheim (DE); Hubert Müllner, Kelkheim (DE); Denes Dudits, Szeged (HU); Attila Feher, Szeged (HU); Katalin Paulovics, Gradna (HU)

(73) Assignee: Hoecht Schering AgrEvo GmbH, Berlin (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

(21) Appl. No.: 09/155,921

(22) PCT Filed: Apr. 8, 1997

(86) PCT No.: PCT/EP97/01741
§ 371 (c)(1),
(2), (4) Date: May 13, 1999

(87) PCT Pub. No.: WO97/38115
PCT Pub. Date: Oct. 16, 1997

(65) Prior Publication Data
US 2002/0035740 A1 Mar. 21, 2002

(30) Foreign Application Priority Data
Apr. 11, 1996 (EP) .......................................... 96105679

(51) Int. Cl.$^7$ ...................... C12N 15/82; C12N 15/31; C12N 5/10; A01H 5/00; A01H 5/10

(52) U.S. Cl. ....................... 800/288; 800/286; 800/290; 800/300; 800/278; 435/69.7; 435/69.8; 435/320.1; 435/418; 435/419

(58) Field of Search ................................ 800/278, 286, 800/288, 290, 300; 435/69.7, 69.8, 320.1, 418, 419

(56) References Cited

U.S. PATENT DOCUMENTS 5,510,471 A 4/1996 Lebrun et al. ............. 536/23.4

FOREIGN PATENT DOCUMENTS

WO    WO 91/11524    8/1991
WO    WO 95/09911    4/1995

OTHER PUBLICATIONS

G Della–Cioppa et al Plant Physiology 84:905–968, 1987.*
Wasmann et al. Mol. Gen. Genet. 205: 466–453, 1986.*
Winnacker, E. p. 540 In: From Genes to Clones, VCH: Weinheim, Fed. Republic of Germany, 1987.*
Buchanan et al. Biochemistry and Mol. Biol. of Plants, pp. 365–367, ASPP : Waldorf, MD, 2000.*
Li et al. Plant Mol. Biol. 23: 401–407, 1993.*
Mol. Gen. Genet.. vol. 236. 1993. pp. 315–325.

* cited by examiner

Primary Examiner—David T. Fox
(74) Attorney, Agent, or Firm—Frommer Lawrence & Haug LLP

(57) ABSTRACT

The invention is drawn to plant cell transformation with a nucleic acid construct comprising a prokaryotic ammonium-specific asparagine synthetase, type A, coding sequence, operably linked to a chloroplast transit peptide-encoding sequence, wherein said plant cells also contain a nucleic acid construct comprising a chloroplastic glutamine synthetase coding sequence in antisense orientation. Plant cells containing both nucleic acid constructs, and plants regenerated therefrom, exhibit improved growth characteristics.

7 Claims, No Drawings

SEQUENCE LISTING

<160> NUMBER OF SEQ ID NOS: 5

<210> SEQ ID NO 1
<211> LENGTH: 15
<212> TYPE: DNA
<213> ORGANISM: Escherichia coli

<400> SEQUENCE: 1
aaaatgaaaa ccgct                                                    15

<210> SEQ ID NO 2
<211> LENGTH: 20
<212> TYPE: DNA
<213> ORGANISM: Artificial Sequence
<220> FEATURE:
<223> OTHER INFORMATION: mutated translational start codon of ASN-A gene
      from Escherichia coli

<400> SEQUENCE: 2
ggcgcatgca gaaaaccgct                                               20

<210> SEQ ID NO 3
<211> LENGTH: 77
<212> TYPE: PRT
<213> ORGANISM: Artificial sequence
<220> FEATURE:
<223> OTHER INFORMATION: Modified transit peptide from small subunit of -continued

```
       Ribulosebiphosphate carboxylase from pea

<400> SEQUENCE: 3

Met Ala Ser Met Ile Ser Ser Ala Val Thr Thr Val Ser Arg Ala
1               5                   10                  15

Ser Arg Gly Gln Ser Ala Ala Val Ala Ser Ser Ser Ala Val Thr Thr
            20                  25                  30

Val Ser Arg Ala Ser Arg Gly Gln Ser Ala Ala Val Ala Pro Pro Gly
            35                  40                  45

Gly Leu Lys Ser Met Thr Gly Pro Pro Val Lys Lys Val Asn Thr Asp
        50                  55                  60

Ile Thr Ser Ile Thr Ser Asn Gly Gly Arg Val Lys Cys
65                  70                  75

<210> SEQ ID NO 4
<211> LENGTH: 57
<212> TYPE: PRT
<213> ORGANISM: Pea

<400> SEQUENCE: 4

Met Ala Ser Met Ile Ser Ser Ser Ala Val Thr Thr Val Ser Arg Ala
1               5                   10                  15

Ser Arg Gly Gln Ser Ala Ala Val Ala Pro Pro Gly Gly Leu Lys Ser
            20                  25                  30

Met Thr Gly Pro Pro Val Lys Lys Val Asn Thr Asp Ile Thr Ser Ile
            35                  40                  45

Thr Ser Asn Gly Gly Arg Val Lys Cys
        50                  55

<210> SEQ ID NO 5
<211> LENGTH: 45
<212> TYPE: PRT
<213> ORGANISM: Pisum Sativum

<400> SEQUENCE: 5

Met Ala Ser Met Ile Ser Ser Ser Ala Val Thr Thr Val Ser Arg Ala
1               5                   10                  15

Ser Arg Gly Gln Ser Ala Ala Val Ala Ser Ser Ser Ala Val Thr Thr
            20                  25                  30

Val Ser Arg Ala Ser Arg Gly Gln Ser Ala Ala Val Ala
            35                  40                  45
```

PROCESS FOR THE PRODUCTION OF PLANTS WITH ENHANCED GROWTH CHARACTERISTICS

RELATED APPLICATIONS

This application is a 371 of PCT/EP97/01741 filed 8 Apr. 1997, which claims priority to European patent application Serial No. 96 105 679.3 filed 11 Apr. 1996. Reference is also made to U.S. application Ser. No. 08/465,526 filed 5 Jun. 1995, now U.S. Pat. No. 5,723,762, which is a divisional of U.S. application Ser. No. 08/360,176 filed 20 Dec. 1994, now U.S. Pat. No. 5,545,819. Each of these U.S. applications and U.S. patents are hereby incorporated herein by reference.

FIELD OF THE INVENTION

The invention relates to: improving plant growth by expression of at least one bacterial asparagine synthetase in the chloroplast and/or plastid of cells of the plant; methods for so improving plant growth including introducing a nucleic acid molecule encoding the bacterial asparagine synthetase into the plant genome (e.g., into plant cells and culturing and/or regenerating the cells into the plants) wherein the nucleic acid molecule is operably linked to a nucleic acid molecule comprising regulatory sequences for expression and for import of the bacterial asparagine synthetase into the chloroplast and/or plastid; and, to plants having such improved growth.

Several documents are cited in the following text. Documents cited herein are hereby incorporated herein by reference.

BACKGROUND OF THE INVENTION

Nitrogen often is the rate-limiting element in plant growth. Most field crops have a fundamental dependence on inorganic nitrogenous fertilizer. Mineral fertilizers are a major source for ground water pollution. Therefore it would be beneficial if plants could utilize the existing nitrogen more efficiently.

Nitrogen is taken up by the plant as inorganic compounds, namely nitrate and ammonia. The majority of this nitrogen is assimilated into organic compounds like amino acids. The enzyme glutamine sythetase plays a major role since it catalyses the assimilation of ammonia into glutamine. Glutamine together with asparagines are the main transport forms of nitrogen in plants. As described in EP 511 979 the expression of a bacterial asparagines synthetases leads to improved growth characteristics which may be enhanced by the additional treatment of the plants with the herbicide glufosinate, a glutamine synthetase inhibitor. Whereas WO 95/09911 describes the production of a plant with improved agronomic or nutritional characteristics by over expression of one or several nitrogen/metabolism enzymes Applicants have now been able to find a quite different way to improve plant growth characteristics.

SUMMARY OF THE INVENTION

It has surprisingly be found that it is possible to improve plant growth capacities by the targeted expression of at least one bacterial asparagine synthetase in the chloroplast.

The present invention is directed to a process for the production of plants with improved growth characteristics which comprises the following steps:

transfer and integration of a DNA sequence coding for a bacterial asparagine synthetases in the plant genome wherein said DNA sequence is linked to regulatory sequences which ensures expression of said gene in a plant cell and leading to the import of the derived protein into the chloroplast and/or plastids of said plant cells and regeneration of intact and fertile plants from the transformed cells.

According to instant invention the term improved growth characteristics is to be understood as encompassing enhanced or faster and more vigorous growth as well as more yield and/or earlier flowering. The process according to instant invention leads also to bigger or more reproductive organs as for example the seeds or bigger or more storage organs as for example tubers.

According to instant invention the bacterial asparagines synthetases may also be expressed directly in the chloroplast by integrating the gene directly into the genome of the chloroplast and/or plastids by for example the biolistic transformation procedure (see U.S. Pat. No. 5,451,513 incorporated herein by reference).

Therefore, the instant invention is also directed to a process for the production of plants with improved growth characteristics which comprises the following steps:

transfer and integration of a DNA sequence coding for a bacterial asparagine synthetases into the genome of the chloroplast and/or plastids of a plant cells, expression of said gene under the control of appropriate regulatory elements and regeneration of intact and fertile plants from the transformed cells.

Surprisingly, it was possible to enhance the growth improving effect even more by reducing the level of the glutamine synthetase expressed in the plant cell.

Accordingly, the instant invention is also directed to processes for the production of plant cells wherein said plant cells express a further gene construct which leads to a reduced level of its endogeneous glutamine synthetase activity.

A "DNA sequence", as the term is used herein, can mean a nucleic acid molecule, e.g., an isolated nucleic acid molecule; and, a "regulatory sequence", as the term is used herein, can mean a nucleic acid molecule which functions to regulate expression and/or import, e.g., import into a chloroplast and/or plastid.

Thus, the invention provides a plant cell containing DNA coding for prokaryotic, e.g., bacterial, asparagine synthetase, e.g., ammonium-specific asparagine synthetase, type A, operably linked to a regulatory sequence for expression of the DNA and import of the asparagine synthetase into the chloroplast and/or plastid of the cell, wherein the cell expresses the asparagine synthetase. Thus, the plant cell expresses the asparagine synthetase in its chloroplast and/or plastid. The plant cell can also contain a construct which provides reduced levels of expression of endogenous glutamine synthetase, e.g., the endogenous gene therefor can be deleted or disrupted.

The invention further provides a method for increasing growth of a plant comprising: transforming a plant cell so that the cell contains DNA coding for prokaryotic, e.g., bacterial asparagine synthetase, e.g., ammonium-specific asparagine synthetase, type A, operably linked to a regulatory sequence for expression of the DNA and import of the asparagine synthetase into the chloroplast and/or plastid of the cell, wherein the cell expresses the asparagine synthetase (e.g., in its chloroplast and/or plastid); and regenerating the plant from the cell. The plant is preferably intact and fertile.

The plant cell in the method can also have the endogenous gene for glutamine synthetase deleted or disrupted, or otherwise expressed at a reduced level. Thus, the method can include transforming a plant cell to have a reduced level of expression of endogenous glutamine synthetase (e.g., by disrupting or deleting the gene therefor) and so that the cell contains DNA coding for prokaryotic, e.g., bacterial asparagine synthetase, e.g., ammonium-specific asparagine synthetase, type A, operably linked to a regulatory sequence for expression of the DNA and import of the asparagine synthetase into the chloroplast and/or plastid of the cell, wherein the cell expresses the asparagine synthetase (e.g., in its chloroplast and/or plastid); and regenerating the plant from the cell. The plant is preferably intact and fertile.

The methods can further comprise treating the plant with a glutamine synthetase inhibitor.

The DNA coding for the asparagine synthetase can be from E. coli. However, from this disclosure, and the documents cited herein, and the knowledge in the art, one skilled in the art can ascertain other genes encoding asparagine synthetase, i.e., asn-A genes, from other microorganisms, e.g. by any routine procedure, for instance:

1. Ascertaining an asn-A gene product activity by routine assays for the asparagine synthetase type A with subsequent purification of the enzyme, e.g., according to Cedar & Schwartz 1969, J. Biol. Chem., 244, 4112–21 and 4122–4127, Humbert & Simoni, 1980, J. Bacteriol., 142, 212–220, and Reitzer & Magasanik, 1982, J. Bacteriol., 151, 1299–1313; see also Herrmann and Somerville, "Amino Acids, Biosynthesis And Genetic Regulation", pp. 137–145 (Addison-Wesley Pub. Co. 1993).
2. Production and purification of polyclonal antibodies against the asn-A gene product according to well-known immunological methods. And,
3. Screening of expression libraries of microorganisms with isolated antibodies against asparagine synthetase type A according to well-known molecular biological methods.

The above-described procedures make it clear that a skilled artisan can obtain asn-A gene sequences from other microorganisms by routine methods. Preferred asparagine synthetase utilizes ammonium ions as an amide donor for the production of asparagine; and thus, preferred DNA encodes such asparagine synthetase. Further, the regulatory sequence can be for a chloroplastic leader peptide; and, the DNA coding for asparagine synthetase and the regulatory sequence can thus encode a prokaryotic asparagine synthetase, e.g., a bacterial asparagine synthetase such as E. coli asparagine synthetase, with a chloroplastic peptide at its N-terminal.

In the methods described herein, the growth of the plant is increased relative to non-transformed plants.

The invention further comprehends a plant, seeds, propagule or propagation material, from the foregoing methods, or containing the foregoing cells.

Additionally, the invention comprehends a gene construct comprising an isolated nucleic acid molecule encoding a prokaryotic, e.g., bacterial, asparagine synthetase, e.g., ammonium-specific asparagine synthetase, type A, operatively linked to a regulatory sequence active in plants for expression of the nucleic acid molecule and import of the asparagine synthetase into the chloroplast and/or plastid of cells of plants, e.g., a chloroplastic leader peptide; and therefore, in an embodiment the invention can provide a gene construct comprising an isolated nucleic acid molecule encoding a prokaryotic, e.g., bacterial such as E. coli, asparagine synthetase with a chloroplastic leader at its N-terminus. The invention also comprehends vectors containing the inventive gene constructs. The vector can be useful for transforming plant cells. Thus, the invention comprehends a plant cell transformed with the gene construct or vector, as well as plants, seeds, and propagules or propagation materials containing such cells.

And, the invention comprehends gene constructs and vectors for reducing endogenous glutamine synthetase expression, e.g., for inserting termination codons after regulatory sequences and prior to coding sequences, or for otherwise disrupting the gene for endogenous glutamine synthetase, as well as cells transformed with such gene constructs or vectors, and plants, seeds and propagules or propagation materials containing such cells.

These and other embodiments are disclosed or are obvious from and encompassed by, the following Detailed Description.

DETAILED DESCRIPTION

A preferred method of introducing the nucleic acid segments into plant cells is to infect plant cells with A. tumefacient carrying an inserted DNA construct. The nucleic acid segments or constructs can be introduced into appropriate plant cells, for example, by means of the Ti plasmid of A. tumefaciens. The T-DNA is transmitted to plant cells upon infection by A. tumefaciens, and is stably integrated into the plant genome. Under appropriate conditions known in the art, the transformed cells develop further into plants.

The Agrobacterium strains customarily employed in the art of transformation are described, for example see especially U.S. Pat. No. 5,188,958 and EP 0 270 615 B1, incorporated herein by reference.

Ti plasmids contain two regions essential for the production of transformed cells. One of these, named transfer DNA (T DNA), induces tumour formation. The other, termed virulent region, is essential for the introduction of the T DNA into plants. The transfer DNA region, which is transferred into the plant genome, can be increased in size by the insertion of the foreign nucleic acid sequence without its ability of transfer being affected. By removing the tumour-causing genes so that they no longer interfere the modified Ti plasmid ("disarmed Ti vector") can then be used as a vector for the transfer of the gene constructs of the invention into an appropriate microspores. In the binary system, to have infection, two plasmids are needed: a T-DNA containing plasmid and a vir plasmid (see especially EP 116718 B1 and EP 120 516 B1).

Besides transformation using Agrobacteria there are many other techniques for the introduction of DNA available. These techniques include, e.g. the protoplast transformation (see EP 164 575) the micro injection of DNA, the introduction of DNA via electroporation as well as biolistic methods and virus mediated infection. From the transformed cells applying suitable media and techniques whole plants can be regenerated (see McCormick et al. (1986) in Plant Cell Reports 5: 81–84). The regenerated plants may be preferably used to cross them with existing breeding lines to improve their growth characteristics as well.

The DNA constructs used in instant invention consist of a transcription initiation region and, under the control of the transcription initiation region, a DNA sequence to be transcribed. The DNA sequence may comprise a natural open reading frame including transcribed 5' and 3' flanking sequences. Alternatively, it may comprise an anti-sense sequence that encodes the complement of an RNA molecule or portion thereof (as described in EP 140 308 B1 and EP 223 399 B1) in order to suppress the expression of the internally expressed glutamine synthetases.

The initiation regions may be used in a variety of contexts and in combination with a variety of sequences. The RNA coded sequences of a gene may be those of a natural gene, including the open reading frame for protein coding and frequently the 5' and 3' untranslated sequences. The RNA translational initiation sequences are included in the constructs, either from the promoter domain or from the attached coding sequences.

Attached to the above sequences are appropriate transcription termination and polyadenylation sequences.

The DNA constructs used in the transformation process according to instant invention may comprise sequences coding for naturally occurring or genetically modified transit peptides (see for example EP 189 707 B1).

Examples of additionally expressed sequences or genes to be expressed from the constructs of the subject invention include:

- especially antisense or sense genes (for gene suppression or cosuppression); as well as additionally
- nutritionally important proteins: growth promoting factors;
- yield enhancing genes or factors, e.g. an invertase gene, a citrate synthase, a polyphosphate kinase;
- proteins giving protection to the plant under certain environmental conditions, e. g. proteins giving resistance to metal or other toxicity;
- stress related proteins giving tolerance to extremes of temperature, freezing, etc.
- proteins of specific commercial value;
- genes causing increased level of proteins, e. g., enzymes of metabolic pathways,
- genes causing increased levels of products of structural value to a plant host, e. g., herbicide resistance, fungus resistance, e.g. chitinase genes, glucanase genes, proteins synthesis inhibitor genes, ribosome inhibitory protein genes, viral resistance, e.g. ribozymes, virus coat protein genes.

The subject constructs will be prepared employing cloning vectors, where the sequences may be naturally occurring, mutated sequences, synthetic sequences, or combinations thereof. The cloning vectors are well known and comprise prokaryotic replication systems, markers for selection of transformed host cells, and restriction sites for insertion or substitution of sequences. For transcription and optimal expression, the DNA may be transformed into plant cells for integration into the genome, where the subject construct is joined to a marker for selection or is co-transformed with DNA encoding a marker for selection.

The selection of transformed cells is enabled by the use of a selectable marker gene which is also transferred. The expression of the marker gene confers a phenotypic trait that enables the selection. Examples for such genes are those coding for antibiotics or herbicide resistance, e.g. genes causing resistance against glutamine synthetases inhibitors, e.g. bialaphos or phosphinothricin resistance conferred by genes isolated from *Streptomyces hygroscopicus* or *viridochromogenes* (BAR/PAT). Other examples are the neomycin phosphotransferase or the glucuronidase gene.

The class of transgenic plants which are covered by this invention is generally as broad as the class of higher plants susceptible to transformation, including both monocotyledonous and dicotyledonous plants. It is known that theoretically all plants can be regenerated from cultured totipotent cells, including but not limited to all major cereal crop species, sugarcane, sugar beet, cotton, fruit and other trees, legumes and vegetables.

Examples of families that are of special interest are Poaceae, but also Solanaceae, Malvaceae and Brassicaceae.

Some suitable species include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Examples of species of commercial interest that can be protected include:

tobacco, *Nicotiana tabacum* L.

tomato, *Lycopersicon esculentum* Mill, potato, *Solanum tuberosum* L.,

Canola/Rapeseed,

*Brassica napus* L., cabbage, broccoli, kale etc.,

*Brassica oleracea* L., mustards *Brassica juncea* L.,

*Brassica nigra* L.,

*Sinapis alba* L. (Brassicaceae), petunia, *Petunia hybrida* (Solanaceae)

sugar beet, *Beta vulgaris*, (Chenopodiaceae), cucumber, Curcurbita sp. (Curcurbitaceae), cotton, Gossypium sp., (Malvaceae), sunflower, *Helianthus annuus,* lettuce *Lactuca sativa,* (Asteraceae=Compositae), pea, *Pisum sativum,* soybean, Glycine max and alfalfa, *Medicago* sp. (Fabaceae=Leguminoseae), asparagus, *Asparagus officinalis;* gladiolus, Gladiolus sp., (Lilaceae);

corn, *Zea mays;* rice, *Oryza sativa* (Poaceae);

wheat, *Triticum aestivum* (Poaceae); and barley, *Hordeum vulgare* (Poaceae).

In an preferred embodiment the invention covers transformed potato, tobacco, corn, sugar beet, cotton, rape seed, soy bean, lupine, rice and wheat. Especially preferred are potatoes.

The invention additionally relates to transformed plants which have been regenerated out of different cell types and which have been transformed according to instant invention.

The transformation can be carried out as described in the following examples, provided by way of illustration only.

EXAMPLES

In general, preparation of plasmid DNA, restriction enzyme digestion, agarose gel electrophoresis of DNA, Southern blots, DNA ligation and bacterial transformation were carried out using standard methods. (Maniatis et al., Molecular Cloning, a Laboratory Manual, Cold Spring Harbor Laboratory (1982), referred to herein as "Maniatis" and hereby incorporated by reference.)

Example 1

Fusion of a bacterial asparagine synthetase gene to the nucleotide sequence for a duplicated chloroplast transit peptide Based on the complete nucleotide sequence of the ASN-A gene from E. coli (Nakamura et al. (1981) or EP 511 979) the gene was cloned as a Hga 1 /Pst 1 fragment into the vector pUC18. By means of PCR based in vitro mutagenesis a Sph1 site was created at the ATG translational start codon changing the nucleotide sequence from AAA ATG AAA ACC GCT (SEQ ID No: 1) into GGC GCATG CAG AAA ACC GCT (SEQ ID No.: 2). This mutation introduced an additional codon for glutamic acid into the gene directly following the ATG translation start codon.

The nucleotide sequence of the modified transit peptide from the small subunit of Ribulosebiphosphate Carboxylase from pea was isolated from the vector pNi6/25 (Wasmann, C. C. et at (1986) Mol. Gen. Genet. 205: 446–453) as a Hind3/Sph1 fragment. As described by Wasmann et al., the pNi6/25 vector was derived by cloning EcoRV-BamHI fragments containing the modified transit peptide sequence into a vector fragment produced from ptac/TPNPTII by digestion with EcoRV and BamHI. The ptac/TPNPTII vector was derived from pTPK1, which was constructed by ligating an EcoRI-BamHI vector fragment from pKM109/15 with the HandIII-BamHI fragment of pTP2 that contains the transit peptide coding sequence and the EcoRI-HindIII fragment of ptac12/Hind that carries the tac promoter. pKM109/15 contains the NPTII gene with an upstream BamHI site. Plasmid pTP2 was derived from pTP1, which carries the EcoRI-SphI fragment of pPSR6 (Cashmore, (1983) In: Genetic engineering of plants—An agricultural perspective; Ed. Kosuge et al. Plenum Publishing, NY, pp. 29–38) that codes for the promoter and transit peptide of the small subunit in pBR327 (Soberon et al. (1980), Gene 9:287–305). The modified transit peptide (SEQ ID NO: 3) contains a duplication of 20 amino acids compared to the natural transit peptide (SEQ ID NO: 4). The 20 amino acid duplication results in increased transport into chloroplasts over that observed with the natural transit peptide (Wasmann et al.).

The sequence of the duplicated transit peptide and ASN-A gene were fused by ligating the Sph1 sites resulting in tpASN. The tpASN gene was exised as a Hind3/Pst1 fragment and after changing the Hind3 site into a Kpn1 site cloned between CaMV 35S promoter and -terminator of the vector pDH51 $^\delta$Kpn.

Example 2

Expression of the tpASN Gene in Tobacco and Rape Seed

The 35S-promoter/tpASN gene/35S-terminator cassette from pDH51 $^\delta$Kpn was isolated as an EcoR1 fragment, Hind3 linkers were added and the fragment was cloned into the Hind3 site of the vector pHOE6/Ac, which confers phosphinothricin resistance to plants. The resulting vector was called pHOE6Ac/tpASN. This vector was transformed into the C58 Agrobacterium strain MP9ORK (Koncz et al., Mol. Gen. Gen., 204, 383–396 (1986)).

Tobacco and rape seed plants were transformed following published procedures. Plants were regenerated on Murashige and Skoog based media.

Transformed plants were selected because of their resistance to the herbicide phosphinothricin (PPT). PPT resistant plants were analysed for the presence of the bacterial asparagine synthetase gene. In a Northern Blot analysis ASN-A specific RNA was detected in the plants. With polyclonal antibodies it is demonstrated that the protein was targeted into the chloroplasts.

Example 3

Expression of the tpASN Gene in Maize

The 35S-promoter/tpASN gene/35S-terminator cassette from pDH51 $^\delta$Kpn was isolated as an EcoR1 fragment, Hind3 linkers were added and the fragment was cloned into the Hind3 site of the vector pB2/35SAc resulting in pB35SAc/tpASN. This vector was used to transform maize protoplasts according to published procedures (EP 511 979 or EP 164 575). Plants were regenerated on Murashige and Skoog based media. Transformed plants were selected because of their resistance to the herbicide phosphinothricin (PPT). PPT resistant plants were analysed for the presence of the bacterial asparagine synthetase gene. In a Northern Blot analysis ASN-A specific RNA was detected in the plants. With polyclonal antibodies it is demonstrated that the protein was targeted into the chloroplasts.

Example 4

Inhibition of Chloroplastic Glutamine Synthetase by Expression of the Antisense Gene in Tobacco and Rape Seed The coding sequences for the chloroplastic isoenzymes of Nicotiana sylvestris and Brassica napus were cloned by PCR methods from the genomic DNA of the respective plants. The resulting fragments were cloned as Apal fragments in antisense orientation between 35S-promoter and -terminator from CaMV located on the vector pRT100. The 35S-promoter/GS-antisense/35S-terminator cassettes were isolated as Pst1 fragments and cloned into the Pst1 site of the vector pHOE6/AcK3. This vector was transformed into the C58 Agrobacterium strain MP9ORK (Koncz et al. supra (1986)). Tobacco and rape seed plants were transformed following published procedures. Plants were regenerated on Murashge and Skoog based media with reduced amounts of ammonia as described.

Transformed plants were selected because of their resistance to the herbicide phosphinothricin (PPT). PPT resistant plants were screened with Southern Blot hybridization for the presence of the ASN-A gene. Southern positive plants were analysed for the inactivation of the chloroplastic glutamine synthetase gene by Northern blots. Plants with the most reduced GS RNA level were selected.

Example 5

Inhibition of Chloroplastic Glutamine Synthetase by Expression of the Respective Antisense Gene in Maize The coding sequences for the chloroplastic isoenzymes of Zea mays, was cloned by PCR methods from the genomic DNA. The resulting fragment was cloned as Apal fragment in antisense orientation between 35S-promoter and terminator from CaMV located on the vector pRT100. The 35S-promoter/GS-antisense/35S-terminator cassette was isolated as Pst1 fragment and cloned into the vector pB2/AcK3.

This vector was used to transform maize protoplasts according to published procedures. Plants were regenerated on Murashige and Skoog based media with reduced amounts of ammonia as described. Transformed plants were selected because of their resistance to the herbicide phosphinothricin (PPT). PPT resistant plants were screened with Southern Blot hybridization for the presence of the ASN-A gene. Southern positive plants were analysed for the inactivation of the chloroplastic glutamine synthetase gene by Northern blots. Plants with the most reduced GS RNA level were selected.

Example 6

Asparagine Content in Transgenic Asparagine Synthetase Expressing Plants

Leaf material from wild type and different ransgenic asparagine synthetase expressing plants was homogenized in buffer. The extracts were run over a Biotronic amino acid analyser. Concentration of the amino acid asparagine were measured and are given in pmol/$\mu$l of extract.

|  | NT-WT | NT-TPASN-2 | NT-TPASN-3 | NT-TPASN-5 | NT-TPASN-11 |
|---|---|---|---|---|---|
| ASN | 586,855 | 890,26 | 3338,5551 | 1506,6314 | 992,0319 |

The concentration of asparagine correlated with the expression of the asparagine synthetase gene as measured on Northern and Western Blots.

Example 7
Production of Transgenic Potato Lines Carrying the Bacterial Asparagine Synthetase Gene The above mentioned construct was used to transform potato plants (Solanum tuberosum L. cv. Desiree 25). The control, non-transformed plant material went through an in vitro regeneration process comparable to the transformants. The tuber tissues were transformed according to the process as described above using the Agrobacterium technology.

The presence of the bacterial asnA gene was proven by hybridization of genomic plant DNAs with a chimeric gene specific fragment. The experiments confirmed that the transformants expressed the transferred gene while the control plants lacked the enzyme.

Northern analysis was carried out by hybridization of total RNA from the transformed potato lines, the hybridization experiment indicated the presence of specific mRNA in the transformants whereas the control plant lines showed again no detectable signal.

Example 8
Growth Behaviour of Transgenic Maize and Tobacco Plants

Transgenic asparagine synthetase expressing plants and transgenic asparagine synthetase expressing plants with reduced glutamine synthetase activity were grown side by side with wild type plants in the greenhouse. The transgenic plants showed a more vigorous growth and flowered earlier than wild type plants.

Field experiments with transgenic potato plants carrying the bacterial asparagine synthetase gene

| Experiment A | | |
|---|---|---|
| Genotype | Tuber weight per plant (gram) | % of control |
| Control plant | 135.0 | 100.0 |
| Trans. As1 | 168.6 | 124.0 |
| Trans. As2 | 182.3 | 135.0 |

| Experiment B | | |
|---|---|---|
| Genotype | Tuber weight per plot (kg) | % of control |
| Control Plant | 8.16 | 100.0 |
| Trans. As1 | 11.39 | 139.5 |
| Trans. As2 | 10.94 | 127.0 |

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. A process for the production of plants with improved growth characteristics, which comprises the following steps:

a) transferring and integrating a nucleic acid encoding a polypeptide comprising an *E. coli* ammonium-specific asparagine synthetase, type A, linked to a chloroplast leader sequence for import of the asparagine synthetase into chloroplasts or plastids of a plant cell, wherein said nucleic acid is operatively linked to a regulatory sequence for expression in said plant cell;

b) transferring and integrating a nucleic acid for expression of an antisense chloroplastic glutamine synthetase RNA comprising transferring and integrating an antisense chloroplastic glutamine synthetase nucleic acid operatively linked to a regulatory sequence for expression of said anti-sense RNA in said cell to make a transformed cell; and c) regenerating intact and fertile plants from the transformed cells, thereby producing plants with improved growth characteristics.

2. A plant cell obtainable by the method of claim 1, comprising:

a) a nucleic acid encoding a polypeptide comprising an *E. coli* ammonium-specific asparagine synthetase, type A, linked to a chloroplast leader sequence for import of the asparagine synthetase into chloroplasts or plastids of a plant cell, wherein said nucleic acid is operatively linked to a regulatory sequence for expression in said plant cell; and b) a second nucleic acid for expression of an anti-sense RNA to an endogenous chloroplastic glutamine synthetase gene comprising a nucleic acid comprising an endogenous chloroplastic glutamine sythetase in an anti-sense orientation operatively linked to a regulatory sequence, said second nucleic acid providing reduced levels of endogenous chloroplastic glutamine synthetase activity upon expression of said anti-sense RNA in said cell.

3. A plant, seed or propagule each containing a cell according to claim 2.

4. A gene construct comprising:
(a) a nucleic acid encoding a polypeptide comprising an *E. coli* ammonium specific asparagine synthetase, type A, linked at its N-terminus to a chloroplastic leader peptide sequence for import of the *E. coli* ammonium-specific asparagine synthetase, type A, into the chloroplasts or plastids of a plant cell, wherein said nucleic acid is operatively linked to a regulatory sequence for expression in said plant cell, and
(b) a second nucleic acid for expression of an anti-sense sequence that encodes an RNA molecule that is complementary to an endogenous chloroplastic glutamine sythetase gene, operably linked to a regulatory sequence for expression of the anti-sense RNA in the plant cell.

5. A gene construct according to claim 4, wherein the *E. coli* ammonium-specific asparagine synthetase, type A, polypeptide is linked at its N-terminus to a modified transit peptide having the amino acid sequence MASMISSSAVTTVSRASRGQSAAVASSSAVTTVSRAS-RGQAAVA(SEQ ID NO:5).

6. A vector comprising the gene construct according to claim 4.

7. A plant cell transformed with the gene construct according to claim 4 or 5, or with the vector according to claim 6.

* * * * *